United States Patent
Janich et al.

(10) Patent No.: US 9,931,082 B2
(45) Date of Patent: Apr. 3, 2018

(54) TIME OPTIMAL PHASE SENSITIVE INVERSION RECOVERY RECONSTRUCTION FOR MAGNETIC RESONANCE IMAGING

(71) Applicant: GENERAL ELECTRIC COMPANY, Schenectady, NY (US)

(72) Inventors: Martin Andreas Janich, Munich (DE); Thomas Kwok-Fah Foo, Niskayuna, NY (US); Anja Christina Sophie Brau, Munich (DE)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 308 days.

(21) Appl. No.: 14/814,671

(22) Filed: Jul. 31, 2015

(65) Prior Publication Data

US 2017/0030990 A1    Feb. 2, 2017

(51) Int. Cl.
*G06K 9/00*     (2006.01)
*A61B 5/00*     (2006.01)
(Continued)

(52) U.S. Cl.
CPC .......... *A61B 5/7285* (2013.01); *A61B 5/055* (2013.01); *G01R 33/5602* (2013.01);
(Continued)

(58) Field of Classification Search
CPC .. A61B 5/055; A61B 5/7285; G01R 33/5601; G01R 33/5602; G01R 33/5611; G01R 33/56563
See application file for complete search history.

(56) References Cited

U.S. PATENT DOCUMENTS 6,559,642 B2    5/2003    King
8,320,646 B2    11/2012    Hu et al.
(Continued)

FOREIGN PATENT DOCUMENTS

EP          0984294 B1    11/2006
WO      2014071249 A1    5/2014
WO      2014072867 A1    5/2014

OTHER PUBLICATIONS

Kellman, Peter, et al. "T2-prepared SSFP improves diagnostic confidence in edema imaging in acute myocardial infarction compared to turbo spin echo." Magnetic resonance in medicine 57.5 (2007): 891-897.*

(Continued)

*Primary Examiner* — Nirav G Patel
(74) *Attorney, Agent, or Firm* — Pabitra K. Chakrabarti (57) ABSTRACT

A system and method for cardiac magnetic resonance imaging (MRI) is disclosed that facilitates the phase sensitive reconstruction of inversion recovery magnetization prepared data with minimal scan time penalty by acquiring the phase reference data with low spatial resolution. The technique can be applied for the investigation of myocardial tissue characterization by acquiring 2D and/or 3D late Gadolinium enhancement (LGE) scans after the injection of a Gadolinium contrast agent. Regional areas of contrast accumulation in scarred myocardial tissue appear bright on these $T_1$-weighted images. As disclosed here the proposed technique for phase sensitive inversion recovery acquisition with low resolution phase reference is robust against changes in inversion time, change in $T_1$ due to Gadolinium contrast washout, high signal-to-noise ratio, and low scan time penalty compared to magnitude LGE.

26 Claims, 7 Drawing Sheets

(51) Int. Cl.
*A61B 5/055* (2006.01)
*G01R 33/56* (2006.01)
*G01R 33/565* (2006.01)
*G01R 33/561* (2006.01)

(52) U.S. Cl.
CPC .... *G01R 33/56563* (2013.01); *G01R 33/5601* (2013.01); *G01R 33/5611* (2013.01)

(56) References Cited

U.S. PATENT DOCUMENTS

| | | | |
|---|---|---|---|
| 8,560,049 | B2 | 10/2013 | Kassai et al. |
| 2010/0195885 | A1 | 8/2010 | Ma |
| 2013/0116545 | A1 | 5/2013 | Xu |
| 2013/0274592 | A1* | 10/2013 | Shin ............... A61B 5/055 600/420 |
| 2014/0113008 | A1 | 4/2014 | Dharmakumar et al. |
| 2014/0200436 | A1 | 7/2014 | Weingärtner et al. |

OTHER PUBLICATIONS

Xue, Hui, et al. "Phase-sensitive inversion recovery for myocardial T1 mapping with motion correction and parametric fitting." Magnetic resonance in medicine 69.5 (2013): 1408-1420.*

Connelly et al. "Multicontrast late gadolinium enhancement imaging enables viability and wall motion assessment in a single acquisition with reduced scan times", Journal of Magnetic Resonance Imaging, vol. 30, Issue: 4, pp. 771-777, Oct. 2009.

Kadbi M et al., "An improved real-time cine Late Gadolinium Enhancement (LGE) imaging method at 3T", Engineering in Medicine and Biology Society, EMBC, 2011 Annual International Conference of the IEEE, pp. 531-534, Aug. 30-Sep. 3, 2011, Boston, MA.

* cited by examiner

TIME OPTIMAL PHASE SENSITIVE INVERSION RECOVERY RECONSTRUCTION FOR MAGNETIC RESONANCE IMAGING

FIELD

Embodiments relate generally to the field of imaging and more particularly to phase sensitive reconstruction inversion recovery magnetic resonance (MR) imaging.

BACKGROUND

Phase sensitive (PS) inversion recovery (IR) has previously been recognized as a method to obtain $T_1$-weighted tissue differentiation with high contrast and relative insensitivity to inversion times (TI). $T_1$-weighted imaging can be achieved by applying IR preparation and waiting a time called inversion time (TI), during which longitudinal magnetization recovers due to $T_1$ relaxation, before acquiring imaging data. These methods require generation of a background phase reference.

Prior strategies for obtaining a phase reference have extracted this information from the image itself or have acquired a separate phase reference image without IR preparation. The first applied single-point Dixon technique (i.e. MRI method used for fat suppression and/or fat quantification) and chemical-shift information from a single echo by calculating phase gradients from neighboring pixels without acquiring phase reference data. The latter achieved PS IR reconstruction by acquiring phase reference data in a separate scan, which was demonstrated in brain imaging.

Figure 1:
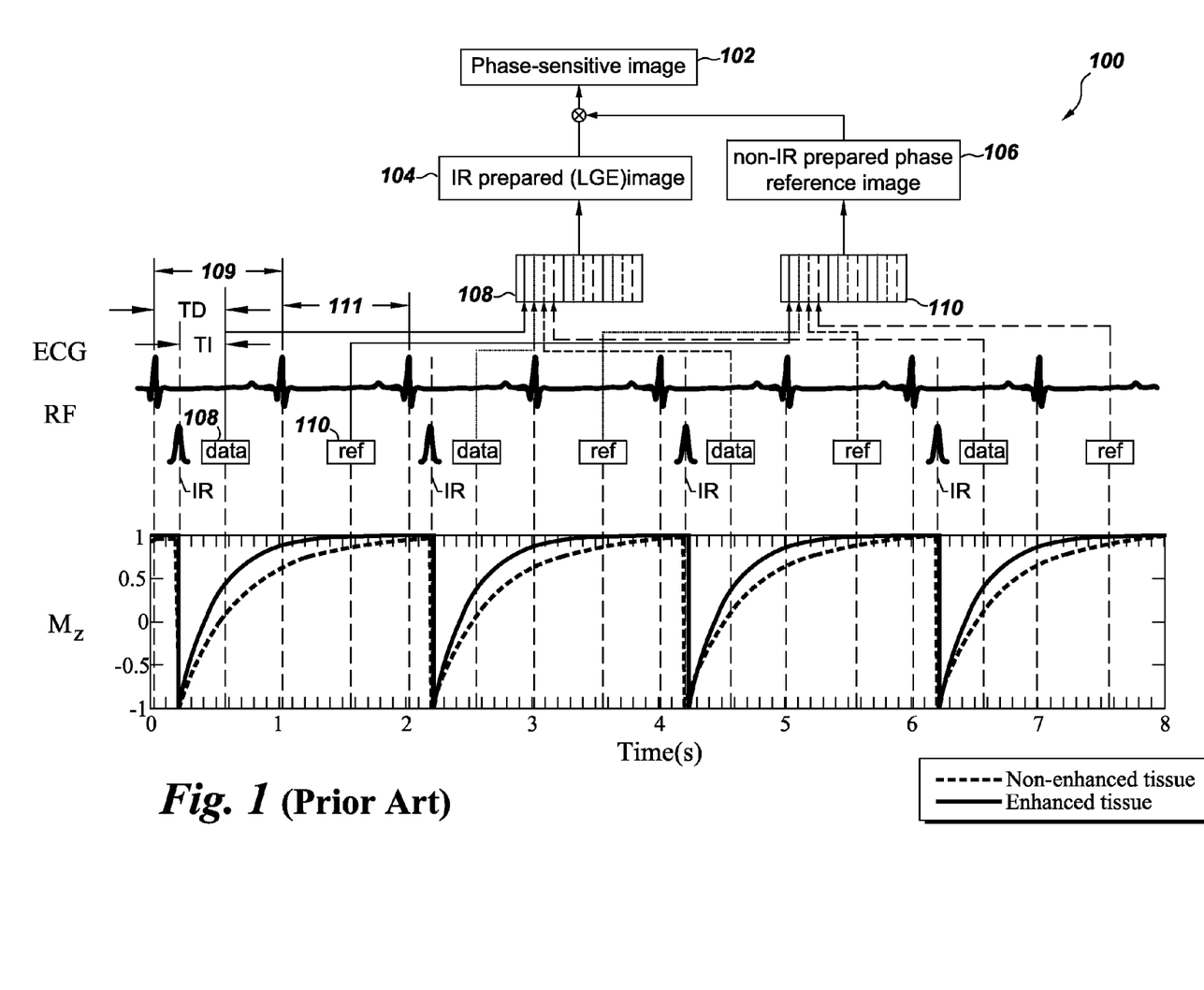
FIG. 1 (PRIOR ART) represents IR-prepared data acquisition and non-IR-prepared phase reference data acquisition interleaved every other cardiac R-R interval, where the same amount of k-space data is acquired for the IR-prepared and phase reference image.

PS IR reconstruction with cardiac gating was proposed for late Gadolinium enhancement (LGE) cardiac MR scans as it is less sensitive to changes in contrast media concentration, especially if the selected TI time is shorter than the optimal TI (null point of healthy myocardial tissue). The system 100 of FIG. 1 (PRIOR ART) demonstrates the previously existing PS LGE image acquisition. Segmented LGE k-space and segmented phase reference k-space are acquired in multiple R-R intervals (i.e., "R-R interval" refers to the duration between subsequent R peaks in an echocardiogram (ECG) waveform, in other words, a heartbeat). However, this PS approach significantly prolongs the total scan time as it requires the use of a 2 R-R interval scan that acquires the primary LGE signal in IR-prepared R-R intervals 109 and phase reference data in non-IR-prepared R-R intervals 111. The phase reference scan is acquired in the non-IR-prepared R-R intervals 111 as it provides sufficient delay after the IR radiofrequency (RF) pulse to allow longitudinal magnetization (Mz) of tissue types to fully recover above the zero line (Mz=0). The phase reference scan is gated to the same cardiac phase as the primary LGE image using a fixed trigger delay (TD) to prevent motion mis-registration. The IR pulse prepared data 108 and phase reference data 110 are interleaved every other R-R interval. The IR prepared image 104 and phase reference image 106 are used to reconstruct a phase sensitive image 102.

The 2 R-R interval prolongs the overall scan time but also yields improved image signal-to-noise ratio (SNR) as the longitudinal magnetization is allowed to more fully recover to the equilibrium value prior to the next IR pulse and data readout. A single R-R interval scan has been proposed for 3D LGE and is used for magnitude (non-PS) image reconstruction. The single R-R scan has the advantage of halved scan time compared to a 2 R-R scan. When used in a 3D volume LGE acquisition, sufficient image SNR from a volume acquisition provides a minimally acceptable image SNR as a trade-off to a much shorter scan time. However, in order to utilize a PS reconstruction, a phase reference measurement needs to be obtained. This phase reference measurement requires that the longitudinal magnetization recover above the zero (Mz=0) line, necessitating a longer, 2 R-R interval.

The present method will address the issues of prolonged scan time, SNR, and longer 2 R-R intervals. The method will desirably allow a more time-efficient acquisition of LGE data that permits the acquisition of the primary normal myocardium-nulled LGE data as well as a phase reference measurement to allow the reconstruction of phase-sensitive inversion recovery images but at a significant reduction in scan time. Furthermore, the improved system will provide a solution that reduces scan time without sacrificing quality of the scan.

SUMMARY

The method of the invention reduces the scan time penalty of PS-IR by acquiring the phase reference image with lower spatial resolution compared to the IR prepared image. The overall scan time is thus marginally increased beyond a scan protocol which acquires IR prepared data in each R-R interval. Further, abrupt transitions in the k-space data are achieved via smooth transitions during acquisition, as based on the order of acquisitions.

The method acquires a PS-IR image in a cardiac gated magnetic resonance acquisition comprising steps of: applying an inversion-recovery magnetization-preparation radiofrequency pulse at a time point within the IR-prepared cardiac R-R interval; awaiting an optimal inversion time (TI) in which a longitudinal magnetization of the tissue of interest recovers at a null point ($M_z=0$) to acquire MR k-space data of tissues within the same IR-prepared cardiac R-R interval; allowing recovery of the longitudinal magnetization above the null point (Mz=0) during the IR-prepared cardiac R-R interval into a different cardiac R-R interval; acquiring phase reference data using a cardiac gated sequence within the non-IR-prepared cardiac R-R interval while limiting spatial resolution to a minimum low spatial resolution, wherein the spatial resolution of the phase reference image is less than the spatial resolution of the IR-prepared image; repeating the steps of acquiring IR-prepared data and acquiring phase reference data through multiple R-R intervals until designated k-space data is acquired, wherein the temporal ordering of the IR-prepared cardiac R-R intervals and the non-IR-prepared cardiac R-R intervals can be sequentially or interleaved in a regular or irregular way; and reconstructing a phase sensitive image using the IR-prepared image and the lower resolution phase reference image.

In one embodiment, a method of acquiring a phase sensitive inversion-recovery (IR) magnetization-prepared image in a cardiac gated magnetic resonance acquisition is disclosed comprising steps of: acquiring IR magnetization-prepared data and reconstructing an IR-prepared image by applying an inversion-recovery magnetization-prepared radiofrequency pulse at a time point within an IR-prepared cardiac R-R interval; awaiting an optimal inversion (TI) time in which a longitudinal magnetization of normal myocardial tissue recovers at a null point ($M_z=0$) to acquire MR k-space data of the tissue within the IR-prepared cardiac R-R interval; acquiring a non-IR-prepared data to reconstruct a non-IR-prepared phase reference image using a cardiac gated sequence within a non-IR-prepared cardiac R-R time interval while limiting spatial resolution to a minimum low spatial resolution, wherein the spatial resolution of the non-IR-prepared phase reference image is less than the spatial resolution of the IR-prepared image; and reconstructing a phase sensitive image using the IR-prepared image and the non-IR-prepared phase reference image. As illustrated, the IR magnetization prepared data is IR magnetization-prepared image k-space data and wherein the non-IR-prepared data is non-IR-prepared reference k-space data.

The method of claim further comprises a step of repeating the steps of acquiring the IR magnetization-prepared image k-space data and acquiring the non-IR-prepared reference k-space data through multiple R-R intervals until designated IR magnetization-prepared image data and non-IR-prepared reference data are acquired, prior to the step of reconstructing the phase sensitive image. The step of repeating performs the steps of acquiring the IR magnetization-prepared image k-space data and acquiring the non-IR-prepared reference k-space data in a hybrid acquisition that combines data from at least two different acquisition intervals. In one aspect, delay times between IR magnetization-prepared radiofrequency pulses that acquire the IR magnetization-prepared image k-space data are a combination of 1 R-R interval and 2 R-R intervals, where $k<k_{min}$ determines a portion of the IR magnetization-prepared image k-space data that is acquired with a delay time of 2 R-R intervals. In another aspect, at least a portion of the IR magnetization-prepared image k-space data is acquired with IR preparation every R-R interval. In addition, a portion of IR magnetization-prepared image data is acquired with IR preparation every R-R interval and another remaining portion of IR magnetization-prepared image k-space data is acquired with IR-preparation every 2 R-R intervals.

Embodiments of the invention implement acquisition of the IR magnetization-prepared image k-space data before or after the step of acquiring the non-IR-prepared reference-space data. The IR magnetization-prepared image k-space data is contrast enhanced in some embodiments, such as when the IR magnetization-prepared image k-space data is late Gadolium enhanced (LGE) to produce an IR-prepared LGE image. In another embodiment, the IR magnetization-prepared image k-space data is acquired after administration of extracellular fraction contrast media to produce a late contrast-enhanced IR magnetization-prepared image, wherein the contrast media are chemical chelates of Gadolinium, Manganese, Dysprosium, super-parametric iron oxide particles, or similar chemical compounds that result in changing tissue $T_1$ or $T_2$ relaxation times. Extracellular fraction (ECF) agents are utilized, as opposed to intravascular agents, as they are safely chelated to a stable structure.

The method allows acquisition of a portion of the IR magnetization-prepared image k-space data at low spatial frequency, with IR preparation every second R-R interval; and a remaining portion of the IR-prepared image k-space data is acquired with IR preparation every R-R interval at high spatial frequency. Additionally, the IR-magnetization prepared image k-space data and non-IR-prepared reference k-space data can be obtained sequentially. In one aspect, the non-IR-prepared image k-space data is not acquired for k-space views of $k>k_{min}$.

A smoothing filter is supplied in the IR magnetization-prepared data of the IR-prepared image at about $k=k_{min}$ to eliminate discontinuities in signal intensities. Acquiring IR magnetization-prepared image k-space data in a transition region around $k=k_{min}$ at multiple times is enabled. For illustrative purposes, the transition region signal intensities around $k=k_{min}$ are averaged in one embodiment. Furthermore, in the step of acquiring IR magnetization-prepared image k-space data image data in the transition region around $k=k_{min}$, TI times vary from TI_A, an optimal TI value for suppressing a signal from a target tissue type in an IR-preparation every second R-R interval, to TI_B, an optimal TI value for suppressing the signal from the target tissue type in the IR-preparation every R-R interval. During the step of acquiring IR magnetization-prepared data, several phase and slab encodings are acquired within the IR-prepared cardiac R-R interval. During the step of acquiring the IR magnetization-prepared data, a cardiac gated sequence can be gated to a respiratory phase. The step of acquiring the non-IR-prepared data can be gated to a respiratory phase as well.

The step of acquiring the non-IR-prepared data generates a multiple receiver coil sensitivity map for recovering image information in reconstructing undersampled k-space acquisitions during parallel image reconstruction. The undersampled k-space acquisitions reduce overall scan time.

In various applications, the method of acquiring a phase sensitive inversion-recovery (IR) magnetization-prepared image in a magnetic resonance acquisition comprising steps of: acquiring IR magnetization-prepared image k-space data to reconstruct an IR-prepared image by applying an inversion-recovery magnetization-prepared radiofrequency pulse within a first time interval; awaiting an optimal inversion (TI) time in which a longitudinal magnetization of a tissue type recovers at a null point ($M_z=0$) to acquire MR image k-space data of a region of the body comprising the tissue type within the first time interval; acquiring non-IR-prepared reference k-space data to reconstruct a phase reference image using a sequence within a different time interval while limiting spatial resolution to a minimum low spatial resolution, wherein the spatial resolution of the phase reference image is less than the spatial resolution of the IR-prepared image; repeating the steps of acquiring the IR magnetization-prepared image k-space data and acquiring the non-IR-prepared reference k-space data through multiple time intervals; and reconstructing a phase sensitive image using the IR-prepared image k-space data and the phase reference image k-space data.

The method further comprises a time interval between IR magnetization-prepared radiofrequency pulses to create a repetition time such that a portion of the IR magnetization-prepared image k-space data is acquired over a shortened time period and the repetition time is longer to acquire remaining IR magnetization-prepared image k-space data to allow for recovery of longitudinal magnetization above $M_z=0$ for other tissues. The remaining IR magnetization-prepared image k-space data can also be acquired to reconstruct the phase reference image of lower spatial resolution.

Various embodiments disclosed may be varied to include features that do not depart from the overall attributes of the invention, the more detailed description of which follows.

DETAILED DESCRIPTION

Various embodiments will be better understood when read in conjunction with the appended drawings. It should be understood that the various embodiments are not limited to the arrangements and instrumentality shown in the drawings.

Cardiac magnetic resonance imaging (MRI) facilitates the investigation to determine whether poorly perfused cardiac tissue is viable and would benefit from revascularization. This can be probed using 2D and/or 3D late Gadolinium enhancement (LGE) scans acquired after the injection of a Gadolinium contrast agent to distinguish healthy versus scarred myocardium. In healthy myocardium, the cardiomyocytes are tightly packed, leaving a small volume for the Gadolinium contrast agent to be distributed. Replacement fibrosis following cardiomyocyte death, however, causes increased extracellular space into which the Gadolinium contrast accumulates. Because Gadolinium causes shortened $T_1$ relaxation time, the regional areas of contrast accumulation in scarred myocardial tissue appear bright on $T_1$-weighted images. This LGE scan is sensitive to the correct selection of the inversion time (TI)), the time between inversion RF pulse (i.e. IR pulse) and image data readout, in order to generate a signal intensity difference between nulled (black) healthy myocardium and enhanced (bright) scar tissue. Selecting the correct TI is especially difficult to achieve for long scan times as the concentration of contrast media in blood and tissue changes with time and is patient dependent, changing the optimal TI during a long scan, e.g. as in high resolution 3D volume scans.

This approach allows a more time-efficient acquisition of PS LGE data that permits the acquisition of the primary normal myocardium-nulled LGE data as well as a phase reference measurement to allow the reconstruction of phase-sensitive inversion recovery (PS-IR) images but at a significant reduction in scan time.

The present method addresses the issues of prolonged scan time, SNR, and longer 2 R-R intervals. The method allows a more time-efficient acquisition of LGE data that permits the acquisition of the primary normal myocardium-nulled LGE data as well as a phase reference measurement to allow the reconstruction of phase-sensitive inversion recovery images but at a significant reduction in scan time. Recent clinical interest has revolved around 3D high spatial resolution LGE imaging for ventricular and atrial wall tissue characterization, which requires a long scan time during free breathing. During the long scan time the Gadolinium contrast agent washes out, leading to a prolongation of the optimal TI. In non-PS LGE imaging this could lead to undesired myocardial tissue contrast due to evolving $T_1$ but fixed TI. For these applications, PS IR can obtain desired image contrast due to relative insensitivity to the evolving $T_1$. The improved system provides a solution that reduces scan time without sacrificing quality of the scan.

Figure 2:
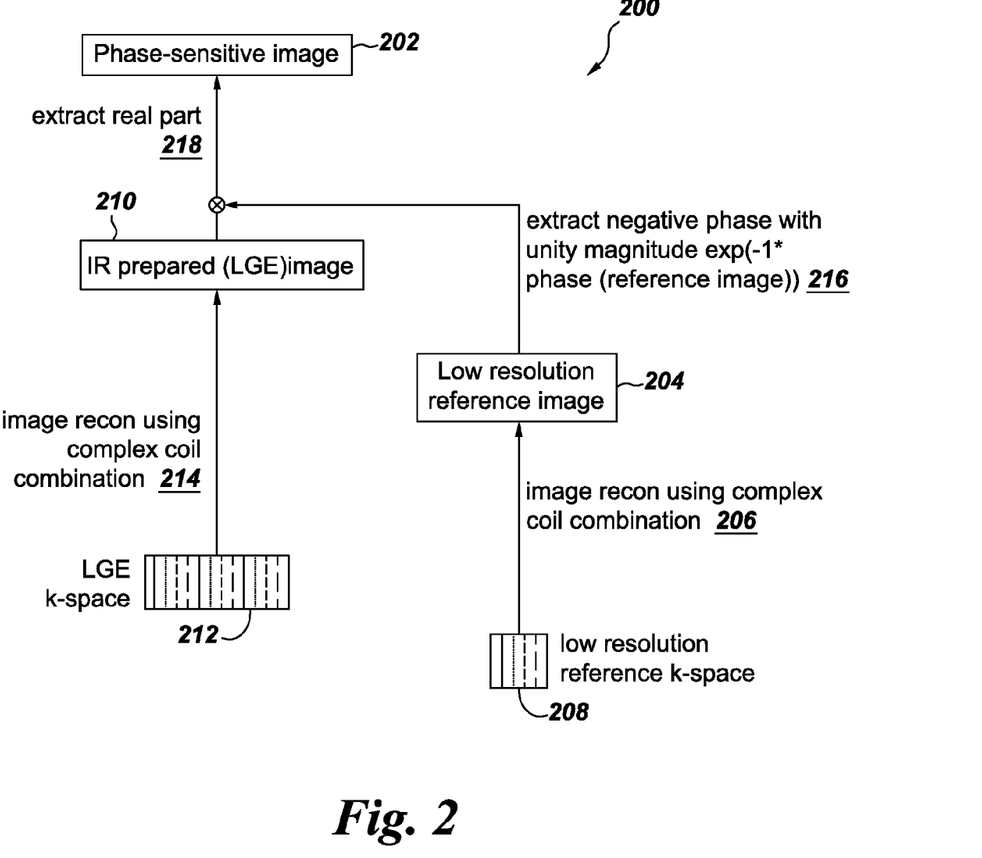
FIG. 2 depicts an embodiment in which high resolution IR-prepared data is acquired along with low resolution non-IR-prepared phase reference data to produce a phase-sensitive image.

In one embodiment of the system 200 in FIG. 2, the scan time penalty of PS-IR is reduced by acquiring the phase reference image 204 with low spatial resolution instead of identical resolution compared to the IR-prepared image. The overall scan time is marginally increased beyond a scan protocol where the IR-prepared data is acquired in each R-R cardiac interval without phase reference data acquisition. Referring to FIG. 2, a low resolution phase reference image 204 is obtained using image reconstruction with complex coil combinations 206 from the low resolution non-IR-prepared phase reference k-space 208. The low resolution non-IR-prepared phase reference k-space 208 can be acquired as segmented over multiple cardiac R-R intervals. Several phase-encode lines and slab-encode lines can be acquired within a single acquisition window within a single cardiac R-R interval without introducing motion artifacts. A high resolution IR-prepared LGE image 210 is obtained by segmenting IR-prepared k-space 212 in multiple IR-prepared cardiac R-R intervals (and reconstructing the image using complex coil combination 214). A negative phase 216 with unity magnitude is extracted from the low resolution phase reference image 204 and multiplied with the IR-prepared LGE image 210; and the real part is extracted at 218 producing the PS image 202.

The non-IR-prepared phase reference data acquisition is timed in different ways within the PS-LGE scan: (a) sequentially before IR-prepared acquisitions, (b) sequentially after IR-prepared acquisitions (See FIG. 3), or (c) interleaved with IR-prepared acquisitions (See FIG. 4). The interleaving can be applied regular or irregular. Overall results present a shortened total scan time as compared to previously existing PS LGE approaches with interleaved IR-prepared and non-IR-prepared data acquisitions.

The low resolution non-IR-prepared phase reference image 204 can also be used as receive coil sensitivities. The overall approach of high-resolution LGE and low-resolution phase reference acquisition may be combined with parallel imaging acceleration as well.

Figure 3:
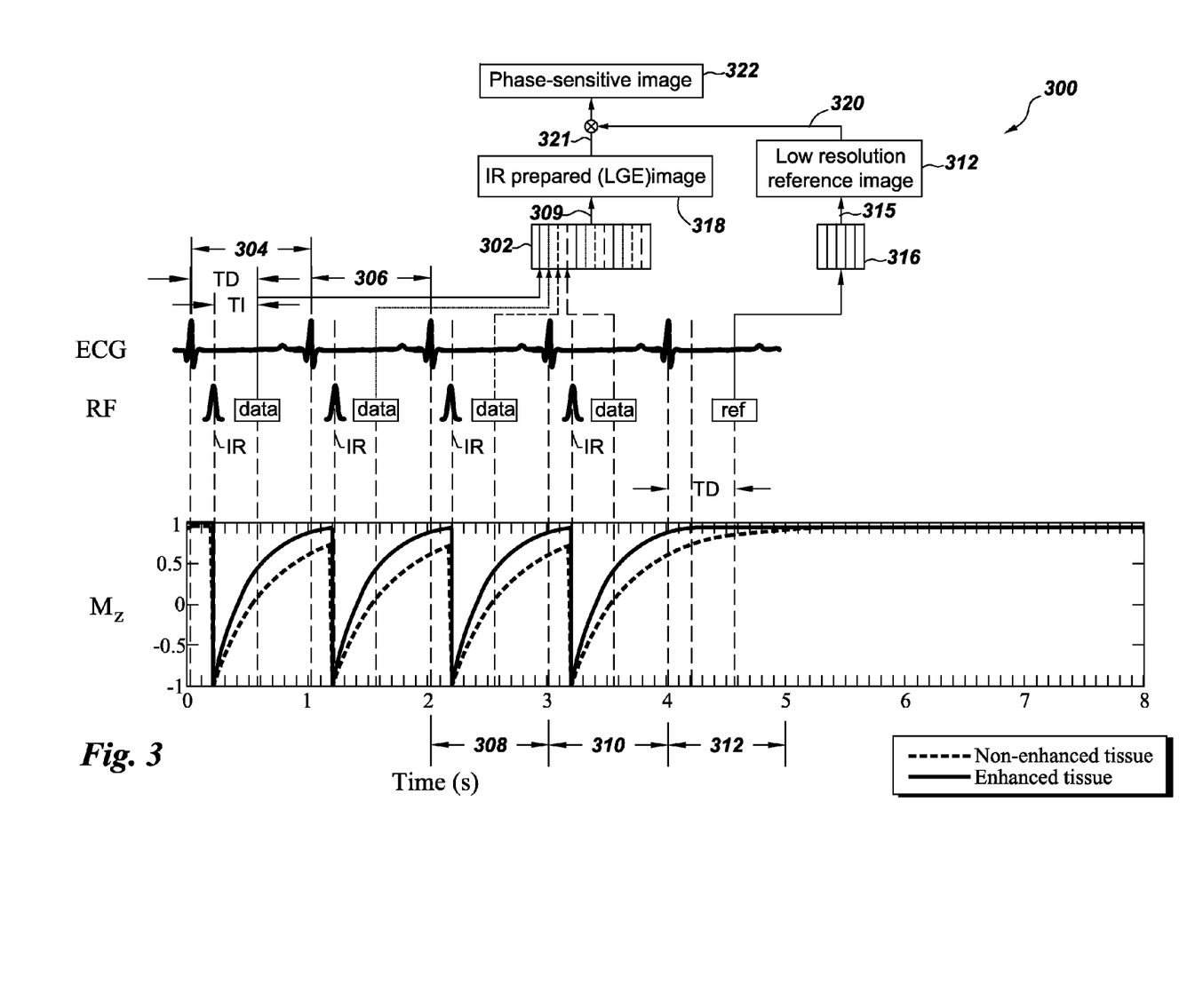
FIG. 3 depicts a timing schematic of the separate IR-prepared and non-IR-prepared cardiac R-R intervals acquired sequentially.

FIG. 3 depicts a timing schematic of the separate IR-prepared and non-IR-prepared cardiac R-R intervals acquired sequentially. A hybrid acquisition is shown wherein some image data is acquired within a single R-R interval and other image data acquired within 2 R-R intervals. In the 2 R-R interval acquisition, the image data acquisition in the first R-R interval is combined with the reference data acquisition in the following, second, R-R interval. Specifically, FIG. 3 depicts the system 300, for exemplary purposes and not limitation, where a high resolution IR-prepared LGE image 318 is acquired via segmenting LGE k-space data 302 by triggering multiple cardiac R-R intervals 304, 306, 308, 310 (and reconstructing the image using complex coil combination 309). Subsequently, a phase reference image 312 is acquired without IR preparation, segmented over multiple cardiac R-R intervals. The low resolution phase reference image 312 is obtained using image reconstruction with complex coil combinations 315 from the low resolution reference k-space data 316. A negative phase 320 with unity magnitude is extracted from the low resolution reference image 312 and multiplied with the IR-prepared LGE image 318; and the real part is extracted at 321 producing the PS image 322.

Figure 4:
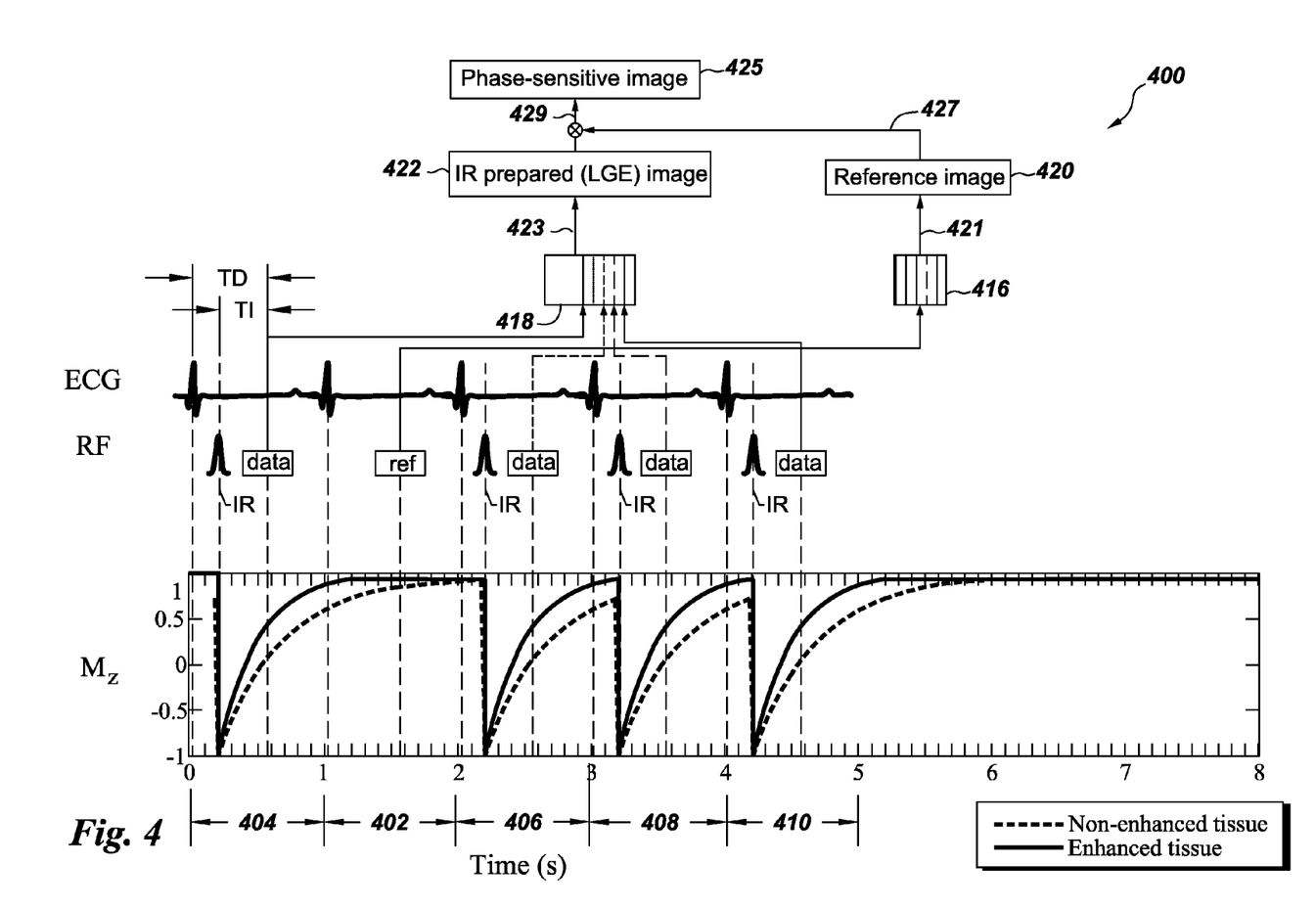
FIG. 4 illustrates a timing schematic of the separate IR-prepared and non-IR-prepared cardiac R-R intervals acquired in an interleaved manner. A hybrid acquisition as in FIG. 3 is used.

FIG. 4 illustrates a system 400 whereby the non-IR-prepared phase reference acquisitions 402 are interleaved with IR-prepared acquisitions 404, 406, 408, 410. The phase reference acquisitions can be segmented over multiple cardiac R-R intervals and interleaved between the IR-prepared cardiac R-R intervals in regular or irregular fashion. Low resolution phase reference k-space data 416 is acquired during the non-IR-prepared cardiac R-R intervals 402 and used to produce the phase reference image 420 (through image reconstruction with complex coil combinations 421). A high resolution IR-prepared (LGE) image 422 is obtained from the LGE k-space data 418, as acquired during the IR-prepared cardiac R-R intervals 404, 406, 408, 410 using image reconstruction of complex coil combinations 423. A negative phase 427 with unity magnitude exp(−i*phase(ref img)) is extracted from the low resolution phase reference image 420 and multiplied with the IR-prepared LGE image 422; and the real part is extracted 429 to produce the PS image 425.

Aspects of the invention utilize appropriate filtering to compensate for different signal weighting ($T_1$-weighting) of mixed IR-prepared data acquisitions where the IR preparation radiofrequency pulse is applied every cardiac R-R interval and mixed with every other cardiac R-R interval in the system 400. Furthermore, the application of the IR preparation radiofrequency pulse every other cardiac R-R interval leads to increased signal to noise ratio (SNR) and contrast to noise ratio (CNR) compared to applying it every cardiac R-R interval.

As the phase reference data can be acquired without IR preparation in a 1 R-R interval scan, the overall increase in scan time for a 3D volume LGE acquisition is:

$$\text{additional\_scan\_time} = R\text{-}R\_\text{interval\_time} * n^{ext}/vps \quad (1)$$

where $n^{ext} = n_y^{ext} * n_z^{ext}$ is the number of phase encodings that define the resolution of the 3D phase reference image and vps is the number of phase encodings performed within one acquisition window (i.e. per cardiac R-R interval). The value for vps is limited by a maximum possible duration of the acquisition window, restricted by the duration in which there is no cardiac motion. The phase encodings can be performed in phase-encode direction (2nd dimension y) and/or the slab-encode direction (3rd dimension z). The primary scan time for a non-phase sensitive 3D LGE acquisition is then:

$$\text{scan\_time} = RR\_\text{interval\_time} * n/vps \quad (2)$$

where $n = n_y + n_z$ is the number of phase encodings in the y and z directions that define the resolution of the 3D LGE image. Generally it is true that $n \geq n^{ext}$. As it can be seen from Eqns. (1) and (2), the additional scan time as a percentage of the actual scan time for a non-phase sensitive 3D LGE scan can be substantially small, and is dependent on the spatial resolution $n^{ext}$ of the phase reference image. Note that a minimum value of $n^{ext}$ provides optimum determination of the phase reference image to ensure an error-free phase sensitive 3D LGE image.

The low spatial resolution limit is determined by the maximum spatial frequency that is acquired for the phase reference data. In one embodiment, the $k_{min}$ is designated as the k-space value to acquire the phase reference data that, when reconstructed to a phase reference image, comprises sufficient spatial resolution to perform a phase correction on the acquired IR-prepared image. Keeping in mind the relationship between image field-of-view (FOV) and k-space where:

$$FOV = \frac{1}{\Delta k} \quad (3)$$

the values of $n_y^{ext}$ and $n_z^{ext}$ are determined from $$n_y^{ext} = \frac{k_{y,min}}{\Delta k_y} \quad (4)$$

$$n_z^{ext} = \frac{k_{z,min}}{\Delta k_z}$$

for a 3D acquisition.

Figure 7:
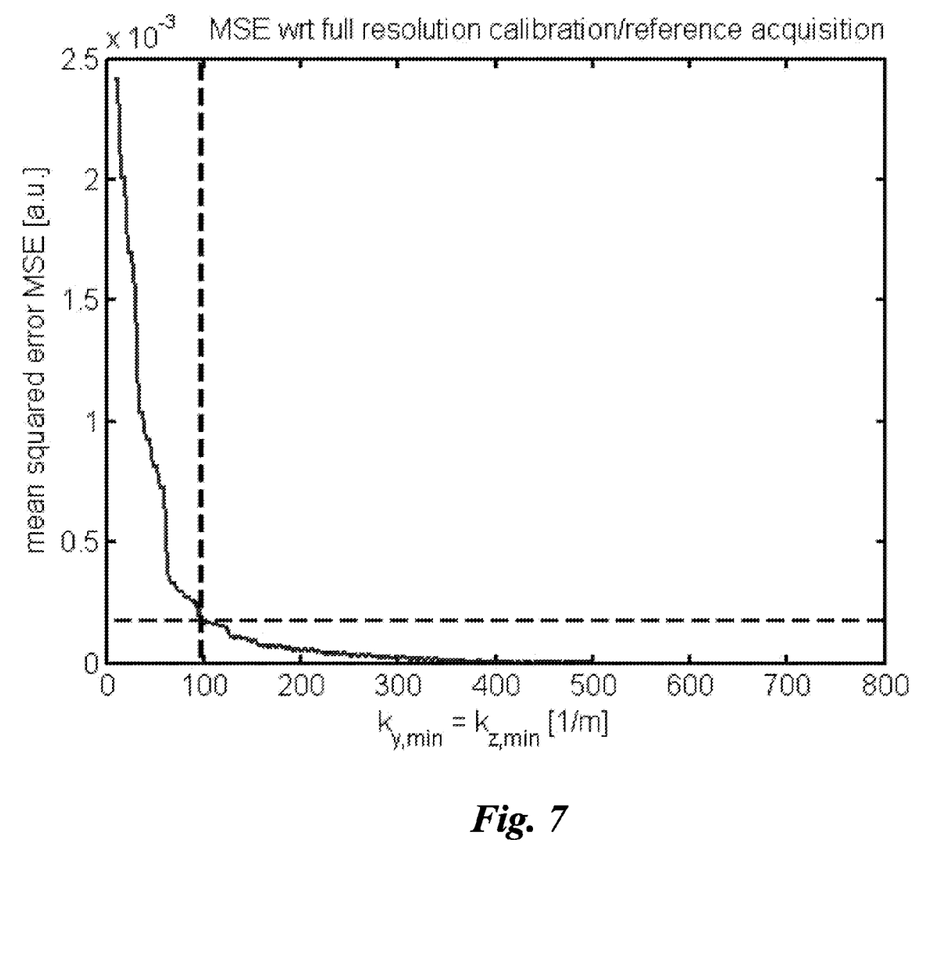
FIG. 7 depicts an embodiment of determining the minimum required spatial resolution for the phase reference data which results in an accurate PS-IR image. The technique uses the mean squared error (MSE) between a PS-IR image with full resolution phase reference and PS-IR image with low resolution phase reference.

The following presents one embodiment of a method to determine the minimum spatial resolution for the phase reference image to obtain an error-free PS IR image. The mean squared error (MSE) between a PS LGE image with full vs. low resolution reference acquisition was examined on a volunteer subject dataset at 3T, as shown in FIG. 7. The result is that the minimum desired spatial resolution for low errors (for example, about MSE≤1.8E−4) is within the region-of-interest (i.e., around the heart) is approximately $k_{y,min} = k_{z,min} \geq 97$ m−1. For field-of-views $FOV_y = 0.300$ m ($FOV_z = 0.064$ m), this results in $n_y^{ext} = 29$ ($n_z^{ext} = 6$). In this embodiment, for exemplary purposes, and not limitation, the additional scan time for PS IR is about 6 R-R intervals. Mean squared error (MSE), however, may be designated at higher and lower values as based upon the region-of-interest.

Other methods may be employed to accomplish finding $k_{min}$; various low spatial resolution limits may be determined as based upon the spatial frequency acquired for the phase reference data. As demonstrated, for example, $k_{min}$ is the k-space value to acquire the phase reference data but may be designated as appropriate where sufficient spatial resolution is identified to perform a phase correction on the acquired IR-prepared image.

Two possible embodiments exist here. The first is to simply acquire a 3D LGE volume acquisition with 1 R-R interval, followed or preceded sequentially by another acquisition for the phase reference scan using 1 R-R intervals without IR preparation. The overall scan time is then:

$$\text{total\_scan\_time} = (RR\_\text{interval\_time} * n^{ext}/vps) + (RR\_\text{interval\_time} * n/vps) \quad (5)$$

This embodiment has a shorter acquisition time than a conventional 2 R-R interval phase sensitive 3D LGE acquisition (total_scan_time=2×RR_interval_time*n/vps). The use of a single R-R interval for the LGE acquisition, however, results in a loss of overall image SNR, an acceptable trade-off for the decrease in overall scan time.

Another embodiment describes a hybrid acquisition where the low spatial frequency k-space data is acquired using 2 R-R intervals for both the LGE images and also the phase reference images. See FIG. 4. In this embodiment the phase reference acquisition is performed in the R-R interval directly and subsequently following an IR-prepared R-R interval, during which LGE data is acquired. It also benefits from the longer longitudinal magnetization recovery time for the LGE acquisition, yielding much higher image SNR and also achieving a shorter scan time as well. The overall scan time for this embodiment is then $$total\_scan\_time = (RR\_interval\_time * next/vps) + (RR\_interval\_time * n/vps) \qquad (6)$$

Note that this embodiment has the added advantage of increased image SNR. Note that for both embodiments several phase and slab encodings can be acquired within a single R-R interval. For example $n_y^{ext}=29$, repetition time TR=4 ms, and parallel imaging acceleration factor 2 results in a readout duration of 60 ms. Therefore we can acquire $n_z^{ext}=2$ slab-encoding steps within a single R-R interval with readout duration of 120 ms. This readout duration is short enough to prevent motion artifacts.

The combination of k-space lines from 1-RR and 2-RR IR prepared acquisitions results in a mixing of signals of different $T_1$-weighting for the LGE image. The present disclosure describes how to deal with this abrupt discontinuity of signal intensities in k-space.

The present idea is to significantly reduce the scan time penalty of PS IR by reducing the spatial resolution of the phase reference acquisition. For example, the scan time penalty compared to the existing 1-RR triggered magnitude PS-IR scan can be 10% but is not limited to this value. Currently, the scan time penalty for PS-IR is 100%, double the total scan time compared to a 1-RR IR prepared LGE scan. The 2 R-R interval scan also has the benefit of higher image SNR.

Figure 5:
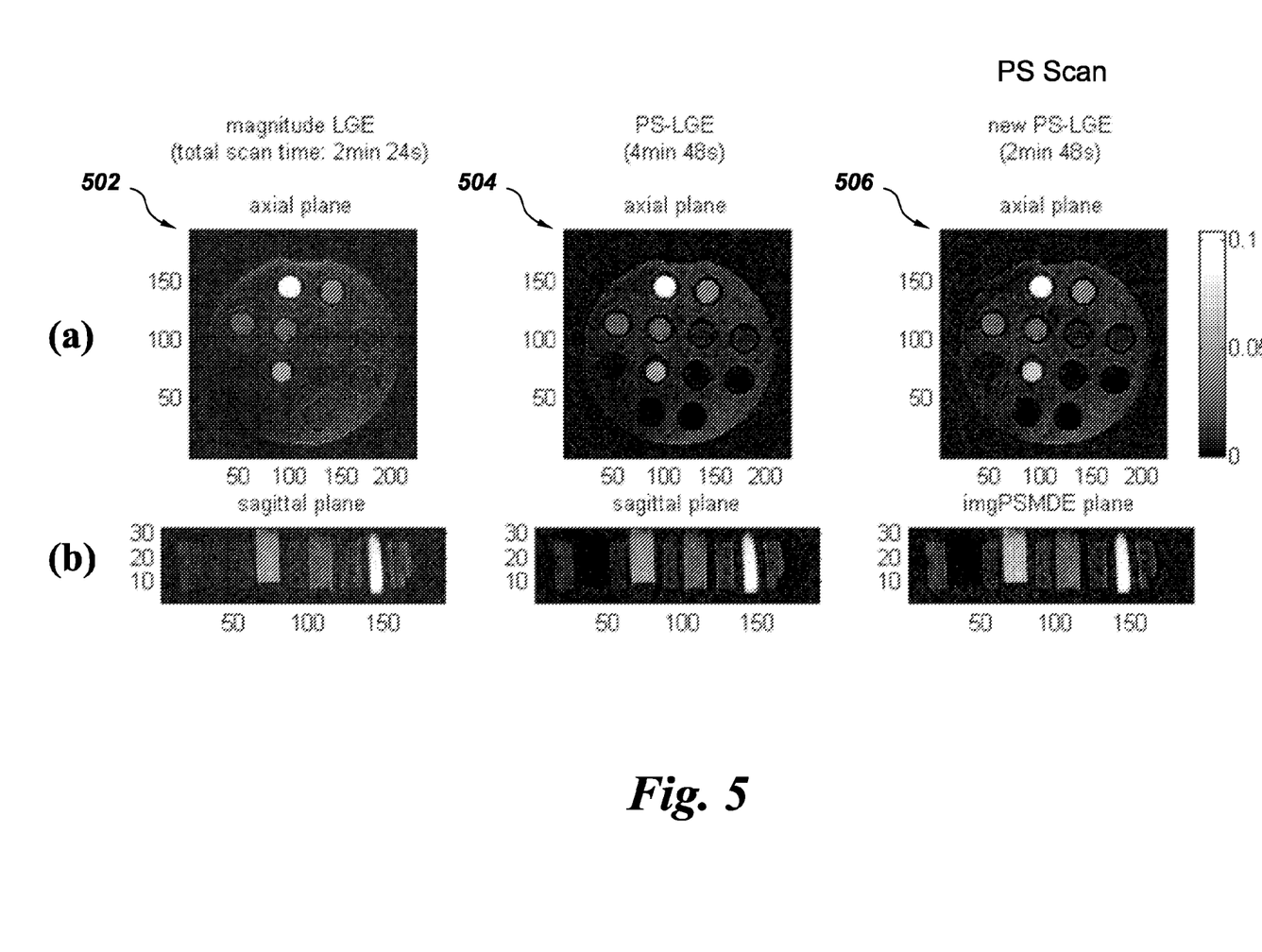
FIG. 5 presents an embodiment of the technique showing data of magnitude LGE, PS-IR with full resolution reference and PS-IR with low resolution phase reference, the latter resulting in a low scan time penalty compared to magnitude LGE.

FIG. 5 demonstrates results of one embodiment of the method using an inversion time (TI) of 240 ms. Axial planes (a) and sagittal planes (b) are presented for a magnitude LGE scan 502 having a total scan time of 2 minutes, 24 seconds; a PS-IR scan with full resolution reference scan 504 with double scan time compared to the magnitude LGE 502 having a scan time of 4 minutes, 48 seconds; and a PS IR scan 506 with low scan time penalty having a scan time of 2 minutes, 48 seconds, about half the time as compared to the full resolution reference scan 504. The PS-IR scans with full resolution reference scan 504 and low resolution reference scan 506 have the same image quality, while the latter image 506 has the benefit of a significantly reduced total scan time.

Figure 6:
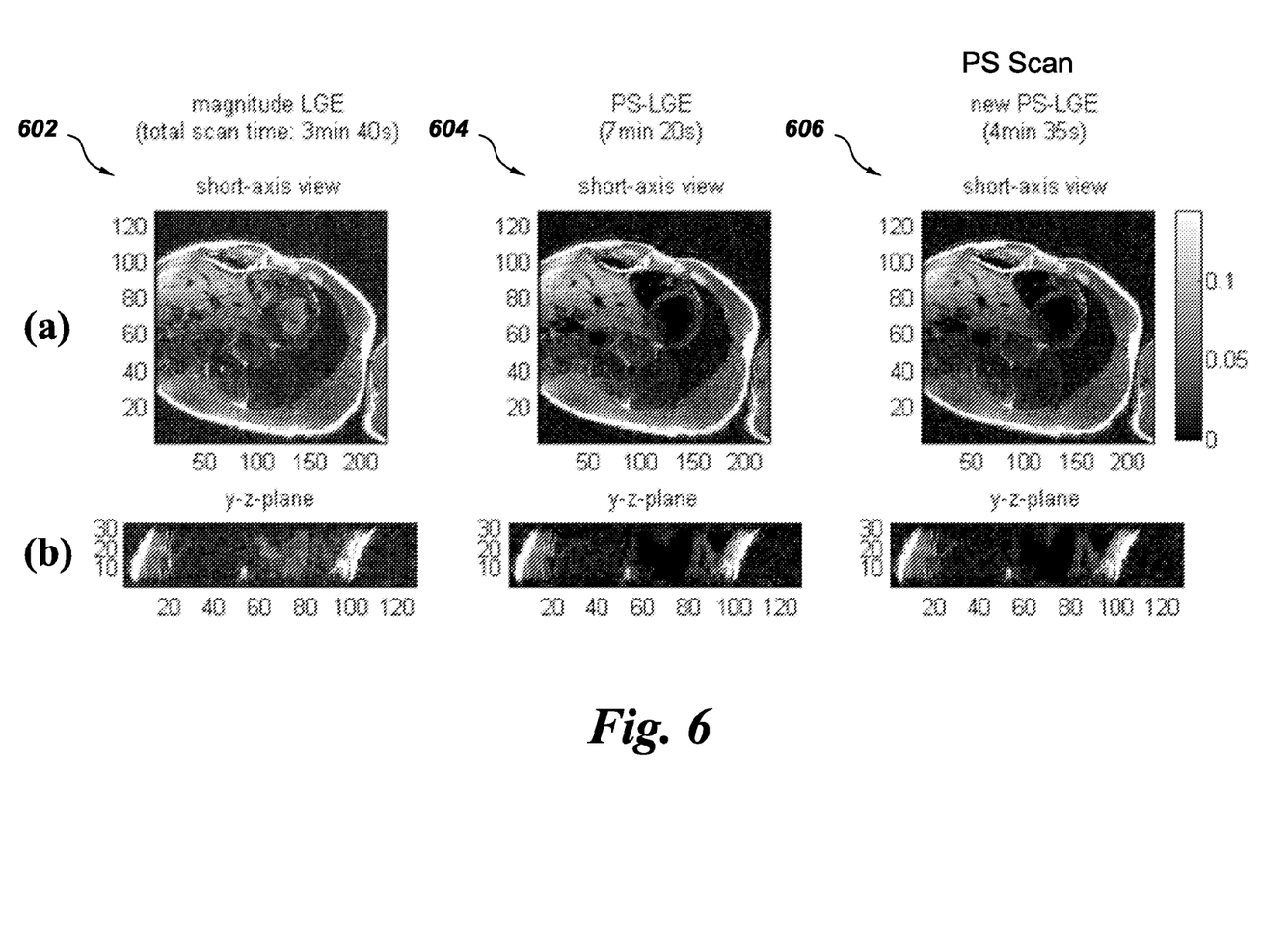
FIG. 6 is another embodiment of the technique showing data from an in vivo scan without Gadolinium contrast injection: magnitude LGE, PS-IR with full resolution reference and PS-IR with low resolution phase reference, the latter resulting in a low scan time penalty compared to magnitude LGE. The total scan time calculations assume a respiratory gating efficiency of 50%.

FIG. 6 portrays (a) short-axis views and (b) orthogonal y-z plane views for a scan of the heart performed without Gadolinium contrast injection. The inversion time (TI) is 340 ms. Magnitude LGE 602 was performed with a scan time of about 3 minutes, 40 seconds. The PS-IR scan with full resolution reference scan 604 took about double the scan time as compared to the magnitude LGE 602. The new PS-LGE scan with low resolution phase reference scan 606 was performed in about 4 minutes, 35 seconds. In comparing the PS-LGE scan with low resolution phase reference 606 to the scan with full resolution reference 604, time was reduced by about half and image quality was similar.

The assumption is that the background phase that needs to be subtracted from the LGE image slowly varies across the image and is smoothly varying, i.e. has low spatial frequency. By presupposing the limited spectral content of the B0 field an assumption frequently made in spiral functional MRI and other field-sensitive applications, the PS LGE acquisition can be accelerated. Hence, it is adequate to acquire a low spatial resolution image for the phase calibration, reference image. In addition, as the image SNR in any MR image is dominated by the low spatial frequency encoding views, if the low spatial frequency encoding views is acquired with a 2 R-R interval acquisition, the overall image SNR for the LGE images is increased without a commensurate additional time penalty (See FIGS. 5 and 6). Hence, acquisition of the low spatial frequency views in the IR-prepared R-R intervals in a 2 R-R interval scan for the LGE acquisition, and similar low spatial frequency encoding views for the phase reference acquisition in the non-IR-prepared R-R intervals in the same 2 R-R interval scan achieves the reduction in scan time for a PS-LGE acquisition as well as improving the overall LGE image SNR. The proposed embodiments are applicable to any PS-IR technique, including but not limited to 2D LGE and 3D LGE. Possible pulse sequence timings of the technique are demonstrated as described prior in FIGS. 3 and 4.

The phase reference acquisition is performed without inversion preparation (in the R-R interval called "non-IR-prepared") or after a sufficiently long interval after an IR magnetization-prepared radiofrequency pulse such that the tissue magnetization is recovered where $M_z>0$. The phase reference acquisition can be performed directly following the IR-prepared acquisition (See FIG. 3), before the IR-prepared acquisition, or interleaved with the IR-prepared acquisition (See FIG. 4). The phase reference acquisition has low spatial resolution and therefore has a short scan time (for example, approximately an additional 12 s for a 2-4 min scan). Due to the low spatial resolution $n^{ext}=n_y^{ext}+n_z^{ext}$ of the phase reference scan, several phase and slab encodings can be performed within a single R-R interval. Furthermore, the scan time of the additional reference acquisition remains the same even if the resolution of the IR-prepared image is increased.

Specific to the system 400 of one embodiment (as shown in FIG. 4), the combination of k-space lines from 1-RR and 2-RR IR-prepared acquisitions results in a mixing of signals of different $T_1$-weighting for the LGE image. This may result in image blurring due to the discontinuity of the k-space signal weighting. The image blurring can be mitigated by a variety of techniques designed to smooth out the abrupt discontinuity of signal intensities in k-space. One approach is to apply a smoothing filter over the transition region in k-space to eliminate any abrupt signal intensity discontinuities. Another approach is to oversample a transition region in k-space by acquiring the k-space encoding views in the transition region with both 1 R-R and 2 R-R acquisitions. The signal intensities resulting from the 1 R-R and 2 R-R acquisitions can be computed to determine a tailored, smoothing filter to reduce the overall signal intensity discontinuities while minimizing any noise amplification. Yet another approach may gradually vary the TI time in the k-space acquisition about the transition region so that the signal intensity weightings in k-space smoothly vary, avoiding abrupt transitions. Different approaches can be used but the salient intent is to minimize the k-space signal intensity variations to eliminate or reduce image blurring.

Furthermore, the extra k-space lines acquired for the phase reference image can also be used as self-calibrated receive coil sensitivities for parallel imaging or other reconstructions. Hence, the coil sensitivities used for parallel image reconstruction (or other image reconstruction) represent the coil sensitivities of the subject at the time of the LGE image acquisition rather than that at a different time. This results in the reduction of motion-related artifacts as the coil sensitivities acquired in the proposed embodiment represents the closest state of motion at the time of the LGE image acquisition rather than that of a different motion state. This allows minimal mis-registration of the coil sensitivity data with the LGE data, a situation that often results in image reconstruction artifacts that degrade the diagnostic quality of the LGE acquisition. This embodiment can be combined with other methods to reduce the total scan time, including but not limited to parallel imaging (e.g., SENSE, GRAPPA) and compressed sensing.

A further benefit of a self-calibrated receive coil sensitivity is that the duration of the LGE acquisition window is shortened because the extra k-space lines needed for calibration are acquired in a different heartbeat, reducing blurring artifacts.

An additional benefit of this technique is that the SNR of the phase reference acquisition is higher compared to the IR-prepared acquisition and therefore the quality of an auto-calibrated parallel imaging reconstruction can be improved.

Aspects of the system and method described herein provide improvements in the art. The PS-LGE scan is sensitive to the correct selection of the inversion time (TI). The correct TI selection is patient dependent and is especially challenging for long scans, e.g. 3D scans, because the Gadolinium contrast washes out during the scan and therefore the optimal TI changes (increases during the scan). As disclosed here, the method makes the scan robust against contrast washout while having a very low scan time penalty. Prior PS-IR techniques double the total scan time (compared to 1-RR IR prepared LGE) and, therefore, are rarely used clinically for high resolution 3D LGE scans.

Aspects of the application described herein have technical and commercial advantages to provide greater patient comfort due to reduced scan time penalty, lowering the likelihood of having to repeat scans, and improving overall image quality. The SNR and contrast-to-noise is increased compared to a 1-RR IR-prepared MDE scan. Further, clinical usability of PS-IR is extended from 2D to long 3D scans.

Clinically, PS-LGE can be further utilized to address additional medical inquiries, including atrial scar imaging which utilizes high spatial resolution and long scan time.

As tested on a 3T MR system on objects with different $T_1$ relaxation values and a non-contrast enhanced in vivo scan, the comparison between 1-RR IR-prepared PS-LGE with a full resolution phase reference and the disclosed technique with a low resolution phase reference had equivalent image quality but with the benefit of significantly reduced scan time. The comparison is shown in FIG. 6 between high resolution IR-prepared LGE with a low resolution phase reference 604, and IR-prepared acquisition with low resolution phase reference 606.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The invention claimed is:

1. A method of acquiring a phase sensitive inversion-recovery (IR) magnetization-prepared image in a cardiac gated magnetic resonance acquisition comprising steps of:
   acquiring IR magnetization-prepared data and reconstructing an IR-prepared image by applying an inversion-recovery magnetization-prepared radiofrequency pulse at a time point within an IR-prepared cardiac R-R interval;
   awaiting an optimal inversion (TI) time in which a longitudinal magnetization of normal myocardial tissue recovers at a null point ($M_z=0$) to acquire MR k-space data of the tissue within the IR-prepared cardiac R-R interval;
   acquiring non-IR-prepared data to reconstruct a non-IR-prepared phase reference image using a cardiac gated sequence within a non-IR-prepared cardiac R-R time interval while limiting spatial resolution to a minimum low spatial resolution, wherein the spatial resolution of the non-IR-prepared phase reference image is less than the spatial resolution of the IR-prepared image;
   reconstructing a phase sensitive image using the IR-prepared image and the non-IR-prepared phase reference image; and
   reducing a scan time penalty associated with the phase sensitive inversion-recovery and thereby providing greater comfort to a patient.

2. The method of claim 1, wherein the IR magnetization prepared data is IR magnetization-prepared image k-space data and wherein the non-IR-prepared data is non-IR-prepared reference k-space data.

3. The method of claim 2, further comprising a step of repeating the steps of acquiring the IR magnetization-prepared image k-space data and acquiring the non-IR-prepared reference k-space data through multiple R-R intervals, prior to the step of reconstructing the phase sensitive image.

4. The method of claim 3, wherein the step of repeating performs the steps of acquiring the IR magnetization-prepared image k-space data and acquiring the non-IR-prepared reference k-space data are a hybrid acquisition.

5. The method of claim 3, wherein delay times between IR magnetization-prepared radiofrequency pulses that acquire the IR magnetization-prepared image k-space data are a combination of 1 R-R interval and 2 R-R intervals, where $k<k_{min}$ determines a portion of the IR magnetization-prepared image k-space data that is acquired with a delay time of 2 R-R intervals.

6. The method of claim 2 further comprising a time interval between IR magnetization-prepared radiofrequency pulses to create a repetition time such that at least a portion of the IR magnetization-prepared image k-space data is acquired at low spatial frequency with IR preparation every R-R interval.

7. The method of claim 6, wherein another portion of IR magnetization-prepared image k-space data is acquired with IR-preparation every 2 R-R intervals at high spatial frequency.

8. The method of claim 2, wherein the IR-magnetization prepared image k-space data and non-IR-prepared reference k-space data are obtained sequentially.

9. The method of claim 2, wherein the IR magnetization-prepared image k-space data is contrast enhanced.

10. The method of claim 9, wherein the IR magnetization-prepared image k-space data is late Gadolium enhanced (LGE) to produce an IR-prepared LGE image.

11. The method of claim 9, wherein the IR magnetization-prepared image k-space data is acquired after administration of extracellular fraction contrast media to produce a late contrast-enhanced IR magnetization-prepared image, wherein the contrast media are chemical chelates of Gadolinium, Manganese, Dysprosium, super-parametric iron oxide particles, or similar chemical compounds that result in changing tissue $T_1$ or $T_2$ relaxation times.

12. The method of claim 3 further comprising a time interval between IR magnetization-prepared radiofrequency pulses to create a repetition time such that a portion of the IR magnetization-prepared image k-space data at low spatial frequency is acquired with IR preparation every second R-R interval and a remaining portion of the IR-prepared image k-space data is acquired with IR preparation every R-R interval at high spatial frequency.

13. The method of claim 2, wherein the non-IR-prepared image k-space data is not acquired for k-space views of $k>k_{min}$.

14. The method of claim 2, further comprising a step of applying a smoothing filter in the IR magnetization-prepared image k-space data of the IR-prepared image at about $k=k_{min}$ such that discontinuities in signal intensities are eliminated.

15. The method of claim 2, further comprising a step of acquiring IR magnetization-prepared image k-space data in a transition region around $k=k_{min}$ at multiple times.

16. The method of claim 15, wherein the transition region signal intensities around $k=k_{min}$ are averaged.

17. The method of claim 2, wherein the step of acquiring IR magnetization-prepared image k-space data image data in a transition region around $k=k_{min}$, TI times vary from TI_A, an optimal TI value for suppressing a signal from a target tissue type in an IR-preparation every second R-R interval, to TI_B, an optimal TI value for suppressing the signal from the target tissue type in the IR-preparation every R-R interval.

18. The method of claim 1, wherein the step of acquiring IR magnetization-prepared data, several phase and slab encodings are acquired within the IR-prepared cardiac R-R interval.

19. The method of claim 1, wherein the step of acquiring the IR magnetization-prepared data is gated to a respiratory phase.

20. The method of claim 1, wherein the step of acquiring the non-IR-prepared data is gated to a respiratory phase.

21. The method of claim 1, wherein the step of acquiring the non-IR-prepared data generates a multiple receiver coil sensitivity map for recovering image information in reconstructing undersampled k-space acquisitions during parallel image reconstruction.

22. The method of claim 21, wherein the undersampled k-space acquisitions reduce overall scan time.

23. A method of acquiring a phase sensitive inversion-recovery (IR) magnetization-prepared image in a magnetic resonance acquisition comprising steps of:

acquiring IR magnetization-prepared image k-space data to reconstruct an IR-prepared image by applying an inversion-recovery magnetization-prepared radiofrequency pulse within a first time interval;

awaiting an optimal inversion (TI) time in which a longitudinal magnetization of a tissue type recovers at a null point ($M_z=0$) to acquire MR image k-space data of a region of the body comprising the tissue type within the first time interval;

acquiring non-IR-prepared reference k-space data to reconstruct a phase reference image using a sequence within a different time interval while limiting spatial resolution to a minimum low spatial resolution, wherein the spatial resolution of the phase reference image is less than the spatial resolution of the IR-prepared image;

repeating the steps of acquiring the IR magnetization-prepared image k-space data and acquiring the non-IR-prepared reference k-space data through multiple time intervals;

reconstructing a phase sensitive image using the IR-prepared image k-space data and the phase reference image k-space data; and reducing a scan time penalty associated with the phase sensitive inversion-recovery and thereby providing greater comfort to a patient.

24. The method of claim 23, further comprising a time interval between IR magnetization-prepared radiofrequency pulses to create a repetition time such that a portion of the IR magnetization-prepared image k-space data is acquired over a shortened time period and the repetition time is longer to acquire remaining IR magnetization-prepared image k-space data to allow for recovery of longitudinal magnetization above $M_z=0$ for other tissues.

25. The method of claim 24, wherein the remaining IR magnetization-prepared image k-space data is also acquired to reconstruct the phase reference image of lower spatial resolution.

26. The method of claim 23, wherein the steps of acquiring IR magnetization-prepared image k-space data and acquiring non-IR-prepared reference k-space data are gated to at least one of a cardiac phase or a respiratory phase, alone or in combination.

* * * * *